(12) United States Patent
Griffiths et al.

(10) Patent No.: US 7,259,249 B2
(45) Date of Patent: Aug. 21, 2007

(54) METHOD FOR PREPARING CONJUGATES OF PROTEINS AND CHELATING AGENTS

(75) Inventors: Gary L. Griffiths, Morristown, NJ (US); Serengulam V. Govindan, Summit, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 11/000,500

(22) Filed: Dec. 1, 2004

(65) Prior Publication Data

US 2005/0191239 A1 Sep. 1, 2005

Related U.S. Application Data

(60) Provisional application No. 60/526,044, filed on Dec. 1, 2003.

(51) Int. Cl.
C07K 1/00 (2006.01)
(52) U.S. Cl. .......................................... 530/400; 514/6
(58) Field of Classification Search .................... None
See application file for complete search history.

(56) References Cited

U.S. PATENT DOCUMENTS 5,106,955 A * 4/1992 Endo et al. ............... 530/391.1
2003/0124057 A1* 7/2003 Griffiths et al. ............ 424/1.49

OTHER PUBLICATIONS

Ruble, et al., Int. J. Radiation OntologyBiol. Phys., 1996, 34, 609-616.*
Timkovich, Analytical Chemistry, 1977, 79, 135-143.*
[Retrieved from] "http://machaut.uchicago.edu/cgi-bin/WEBSTER.sh?WORD=subsequently"2007, 1 page [Retrieved on Feb. 28, 2007].*
Ruble, Gaye, et al., "The Use of 212Pb-Labeled Monoclonal Antibody in the Treatment of Murine Erythroleukemia" Int. J. Radiation Oncology Biol. Phys., vol. 34, No. 3, pp. 609-616, 1996.
Timkovich, Russell, "Detection of the Stable Addition of Carbodiimide to proteins," Analytical Biochemistry 79, 135-143 (1977).
Brinkley, Michael, "A Brief Survey of Methods for Preparing Protein Conjugates with Dyes, Haptens, and Cross-Linking Reagents" Teaching Editorial Bioconjugate Chem., vol. 3, No. 1, 1992.
Lewis, Michael R., "A Facile, Water-Soluble Method for Modification of Proteins with DOTA. Use of Elecvated Temperature and Optimized pH to Achieve High Specific Activity and High Chelate Stability in Radiolabeled Immunoconjugates" Bioconjugate Chem. 1994, 5, 565-576.

Govindan, Serengulam V., "90Yttrium-Labeled Complementarity—Determining-Region-Grafted Monoclonal Antibodies for Radioimmunotherapy: Radiolabeling and Animal Biodistribution Studies" Bioconjugate Chemistry reprinted from vol. 9, No. 6, pp. 773-782.
Carraway, Kermit L., et al., "Short Communication: Reaction of tyrosine residues in proteins with carbodiimide reagents" Biochim. Biophys. Acta, 160 (1968) 272-274.
Li, Min, et al., "Labeling Monoclonal Antibodies with 90Yttrium—and 111Indium—DOTA Chelates: A Simple and Efficient Method" Bioconjugates Chemistry, Mar./Apr. 1994, vol. 5, No. 2, pp. 101-104.
Griffiths, Gary L., et al., "90Y-DOTA-hLL2: An Agent for Radioimmunotherapy of Non-Hodgkin's Lymphoma" The Journal of Nuclear Medicine, vol. 44, No. 1, Jan. 2003, pp. 77-84.
Meares, Claude, et al., "Conjugation of Antibodies with Bifunctional Chelating Agents: Isothiocyanate and Bromoacetamide Reagents, Methods of Analysis, and Subsequent Addition of Metal Ions" Analytical Biochemistry 142, 68-78 (1984), pp. 68-78.
Kozak, Robert W., et al., "Nature of the Biofunctional Chelating Agent Used for Radioimmunotherapy with Yttrium-90 Monoclonal Antibodies: Critical Factors in Determing in Vivo Survival and Organ Toxicity" Cancer Research 49, 2636-2644, May 15, 1989, pp. 26392644.
Zoghbi, Sami S., et al., "A Modified Procedure for Rapid Labelling of Low Concentrations of Bioactive Proteins with Indium-111" Int. J. Nucl. Med. Biol. vol. 12, No. 3, pp. 159-166, 1985, pp. 159-166.
Esteban, Jose M., et al., "New Method for the Chelation of Indium-111 to Monoclonal Antibodies: Biodistribution and Imaging of Athymic Mice Bearing Human Colon Carcinoma Xenografts" The Journal of Nuclear Medicine, vol. 28, No. 5, May 1987, pp. 861-870.
Harrison, A., et al., "The In Vivo Release of 90Y from Cyclic and Acyclic Ligand—Antibody Conjugates" Nucl. Med. Biol. vol. 18, No. 5, pp. 469-476, 1991.

(Continued)

*Primary Examiner*—Anish Gupta
*Assistant Examiner*—Satyanarayana R. Gudibande
(74) *Attorney, Agent, or Firm*—Faegre & Benson LLP (57) ABSTRACT

Improved synthesis methods are provided for preparing conjugates of proteins and chelating agents. In the synthesis methods, non-stable bonds are hydrolyzed after the conjugate is synthesized, for example by treating the conjugate with a quenching agent. The synthesis method provides conjugates that are substantially free of non-stable bonds between the protein and the chelating agent, such that the chelating agent is less likely to dissociate with the conjugate after the conjugate has been stored for extended periods. The conjugate may be useful for therapeutic or diagnostic methods.

12 Claims, 3 Drawing Sheets

OTHER PUBLICATIONS

Hnatowich, D. J., et al., "The Preparation of DTPA-Coupled Antibodies Radiolabeled with Metallic Radionuclides: an Improved Method" Journal of Immunological Methods, 65 (1983) 147-157.

Sharkey, Robert M., et al., "Sselection of a DTPA Chelate Conjugate for Monoclonal antibody Targeting to a Human Colonic tumor in Nude Mide" Int. J. Cancer: 46, 79-85 (1990).

Stimmel, Julie B., et al., "Yttrium-90 Chelation Properties of Tetraazatetraacetic Acid Macrocycles, Diethylenetriaminepentaacetic Acid Analogues, and a Novel Terpyridine Acyclic Clelator" Bioconjugate Chem. 1995, 6, pp. 219-225.

Cummins, Clark H., et al., "A Convenient Sysnthesis of Bifunctional Chelating Agents Based on Diethylenetriaminepentaacetic Acid and Their Coordination Chemistry with Yttrium (III)" Technical Notes Bioconjugate Chem. 1991, 2, 180-186.

Chinn, Paul C., et al., "Preclinical evaluation of 90Y-labeled anti-CD20 monoclonal antibody for treatment of non-Hodgkin's lymphoma" International Journal of Oncology 15: 1017-1025, 1999.

Stimmel, Julie B., et al., "Yttrium-90 Chelation Properties of Tetraazatetraacetic Acid Macrocycles, Diethylenetriaminepentaacetic Acide Analogues, and a Novel Terpyridine Acyclic Chelator" Bioconjugate Chem., 1995, 6, 219-225.

Deshpande, Shrikant V., et al., "Yttrium-90-Labeled Monoclonal Antibody for Therapy: Labeling by a New Macrocyclic Bifunctional Chelating Agent" The Journal of Nuclear Medicine, vol. 31, No. 4, Apr. 1990, pp. 473-479.

* cited by examiner

Figure 1. SE-HPLC analysis of Y-90-labeling of non-repurified hLL2-DOTA

Figure 2. SE-HPLC analysis of Y-90-labeling of purified hLL2-DOTA

Figure 3. Coupling of DOTA to hLL2 Antibody at Lysine Residues

METHOD FOR PREPARING CONJUGATES OF PROTEINS AND CHELATING AGENTS

This application claims priority to U.S. Provisional Application No. 60/526,044, filed Dec. 1, 2003, the contents of which are incorporated herein in their entirety.

BACKGROUND

Metal ions, such as radionuclides and transition metals, are useful for many diagnostic and therapeutic techniques. For example, metal ions can be used as diagnostic or therapeutic agents, particularly with regard to radioimmunodetection, radioimmunotherapy, magnetic resonance imaging, photodynamic therapy or other similar modalities. However, these techniques require specific targeting of the metal ion to a selected tissue. Targeting molecules (such as antibodies or binding molecules) and/or targetable molecules (such as haptenic peptides) can be used to target metal ions to selected tissues, where the targeting molecule or targetable molecule is conjugated to a chelator. Antibody-chelator conjugates (or peptide-chelator conjugates) are useful because the chelator moiety of these conjugates can bind metal ions to form a metal chelate.

Antibody-chelator conjugates can be used to directly target the metal chelate to a targeted tissue., whereas peptide-chelator conjugates are typically used in combination with a bi-specific binding molecule. For example, the peptide-chelator conjugates may include a hapten that is recognized by a bi-specific binding molecule that also recognizes the targeted tissue. As such, the bi-specific binding molecule can be used to localize the peptide-chelator conjugate (i.e., the targetable molecule) to the targeted tissue.

The stability of these conjugates is important, because if the chelator becomes disassociated from the antibody or peptide, the free chelator can compete with the conjugate for binding to the diagnostic or therapeutic metal ion. Ultimately, this results in a lower percentage incorporation of the metal ion into the antibody- or peptide-chelator conjugate.

As such, there is an ongoing need to prepare stable conjugates of chelating agents and metal chelates with proteins, polymers, polypeptides and peptides, such that the synthesized conjugates remain useful for high incorporation of metals, over an extended period of time. One must ensure that the chelating agent is able to stably and reproducibly bind to a metal ion of interest, and continue to do so in a high incorporation yield, over an extended period of time after manufacture of the chelator-protein conjugate. By incorporating a quenching step into the conjugate synthesis reaction, the inventors have addressed a problem concerning shelf-life stability of chelator-protein conjugates, (e.g., those produced by acylation reactions on protein amino groups).

Previously, others have used quenching steps in synthesis reactions, for example, to treat peptide-methotrexate conjugates. See Endo et al, U.S. Pat. No. 5,106,955; see also Brinkley, *Bioconjugate Chem.* 1992, Vol. 3, No. 1, pp. 1-13. However, quenching steps have not been previously used to treat 1,4,7,10-tetraaazacyclododecane N,N',N",N'"-tetraaacetic acid (DOTA)-peptide conjugates or derivatives thereof. See Lewis et al., Bioconjugate Chem. 1994, 5, 565-576; Govindan et al., Bioconjugate Chem., Vol. 9, No. 6, 1998, 773-782; Min et al., Bioconjugate Chem. Vol. 5, No. 2, 1994,101-104; U.S. Pat. No. 5,082,930; U.S. Pat. No. 5,435,990; U.S. Pat. No. 5,739,323; and U.S. Pat. No. 5,756,065.

Most methods of synthesizing DOTA-peptide conjugates rely on formation of stable amide bonds between the DOTA molecule and one or more ϵ-amino groups on a lysine residue of the peptide. Although the previously described methods of forming DOTA-peptide conjugates may also result in the formation of unstable DOTA-ester bonds with the peptide, (e.g., at the hydroxyl group of a serine, threonine, or tyrosine), because DOTA-peptide synthesis reactions are typically performed at a high pH (>8.0), any unstable ester bonds would be expected to be readily hydrolyzed. Further, DOTA-peptide synthesis reactions typically result in a low substitution ratio of DOTA per peptide. For example, a synthesis reaction using a molar ratio of DOTA to peptide of ~100:1 typically results in a substitution ratio of less than four (4) DOTA molecules per peptide in the synthesized conjugate. See Lewis et al., Bioconjugate Chem. 1994, 5, 565-576; and Govindan et al., Bioconjugate Chem., Vol. 9, No. 6, 1998; see also Griffiths et al., J. Nucl. Med. Vol. 44, No. 1, January 2003, 77-84. The low substitution ratio would suggest that the synthesized DOTA-peptide conjugate contains few unstable bonds (e.g., serine, threonine, and/or tyrosine esters) relative to stable bonds (e.g., lysine amides). As such, it would not be expected that the incorporation of a quenching step would significantly improve the stability and hence, the labeling efficiency, of DOTA-peptide conjugates stored over a period of time.

SUMMARY

Disclosed herein is a method of preparing a conjugate that includes reacting a chelating agent and a protein or peptide to form the conjugate, and subsequently reacting the conjugate with a quenching agent. Typically, the conjugate is formed by an amino acyl reaction. In one embodiment, the chelating agent is activated by reacting the chelating agent with an acylating reagent before, simultaneously, or after reacting the chelating agent and the protein to form the conjugate. Preferably, the chelating agent is reacted with an acylating reagent before reacting the chelating agent and the protein. The activated chelating agent may include an acyl azide, an acyl cyanide, an acyl halide, an activated acyl ester, an enol ester, an isoxazolium agent, an isothiocyanate, an N-acyl imidazole, an N-acyl pyrazole, an N-acyl triazole, a carbodiimide, a mixed carbonic anhydride, a mixed carboxylic anhydride, a mixed phosphinic anhydride, a mixed phosphonic anhydride, or a mixture of the aforementioned compounds.

The quenching agent typically includes a nucleophilic agent. For example, the quenching agent may include an ammoniacal solution, an alkyl or aryl amine, an alkyl or aryl hydroxamate, a hydroxylamine or hydroxylamine derivative or salt thereof (e.g., hydroxylamine hydrochloride or another hydroxylamine-acid salt), or mixtures of these compounds. A hydroxylamine derivative may be, for example, an O-substituted hydroxylamine such as an O-alkyl hydroxylamine or the like. Other substituted hydroxylamines are known in the art.

The chelating agent may include an acyclic or cyclic multi-carboxylic acid derivative. Suitable chelating agents include but are not limited to DOTA, DTPA, TETA, DOTP, EDTA, DOTMA, DOP3, or derivatives of these chelating agents. Preferably, the chelating agent comprises DOTA.

The chelating agent may be used to chelate any useful metal species. In particular, the chelating agent may be used to chelate a radionuclide, and as such, the conjugate be radiolabeled. Useful radionuclides may include $^{47}$Sc, $^{51}$Mn, $^{52}$Mn, $^{52}$Fe, $^{59}$Fe, $^{55}$Co, $^{62}$Cu, $^{64}$Cu, $^{67}$Cu, $^{67}$Ga, $^{68}$Ga, $^{72}$As, $^{77}$As, $^{83}$Sr, $^{89}$Sr, $^{86}$Y, $^{89}$Zr, $^{90}$Y, $^{94}$Tc, $^{94}$mTc, $^{99}$Mo, $^{99}$mTc, $^{105}$Pd, $^{105}$Rh, $^{111}$Ag, $^{110}$In, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$LU, $^{177}$Lu, $^{186}$Re, $^{188}$Re, $^{189}$Re, $^{194}$Ir, $^{197}$Pt, $^{198}$Au, $^{199}$Au, $^{211}$At, $^{211}$Pb, $^{212}$Bi, $^{212}$Pb, $^{213}$Bi, $^{223}$Ra, $^{225}$Ac, or combinations of these radionuclides.

Any useful protein may be used to prepare the conjugate. Particularly useful proteins include antibodies, antibody fragments, cytokines or immunomodulators, polyproteins, peptides, or a mixture of these exemplary proteins. Where an antibody is used to prepare the conjugate, the antibody may be monoclonal or polyclonal. It may be desirable to select a murine, chimeric, primatized, humanized, or human antibody to prepare the conjugate. Multispecific antibodies (e.g., bi-specific antibodies) or multivalent antibodies may be particular desirable for preparing the conjugates. Trivalent or tetravalent binding molecules may be used.

Typically, where an antibody is used to prepare the conjugate, the antibody or antibody fragment includes at least one arm that specifically binds a targeted tissue, for example targeted tissues that include an antigen associated with a malignant disease, a cardiovascular disease, an infectious disease, an inflammatory disease, an autoimmune disease, or a neurological disease. Specific antigens may include colon-specific antigen-p (CSAp), carcinoembryonic antigen (CEA), CD4, CD5, CD8, CD14, CD15, CD19, CD20, CD21, CD22, CD23, CD25, CD30, CD45, CD74, CD80, HLA-DR, Ia, Ii, MUC 1, MUC 2, MUC 3, MUC 4, NCA, EGFR, HER 2/neu, PAM4, TAG-72, EGP-1, EGP-2, A3, KS-1, Le(y), S100, PSMA, PSA, tenascin, folate receptor, VEGF, PIGF, ILGF-1, necrosis antigens, IL-2, IL-6, T101, MAGE, or a combination of these antiges. In particular, antigens may include carcinoembryonic antigen, tenascin, epidermal growth factor receptor, platelet derived growth factor receptor, fibroblast growth factor receptors, vascular endothelial growth factor receptors, gangliosides, HER/2neu receptors and combinations of these antigens.

The antibody may recognize particular antigens associated with an infectious disease such as a bacterial disease, fungal disease, parasitic disease, viral disease, or combinations of these diseases. Particular infectious diseases may include those caused by a pathogen selected from *Microsporum, Trichophyton, Epidermophyton, Sporothrix schenckii, Cryptococcus neoformans, Coccidioides immitis, Histoplasma capsulatum, Blastomyces dermatitidis, Candida albicans*, human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, *Anthrax bacillus, Streptococcus agalactiae, Legionella pneumophilia, Streptococcus pyogenes, Escherichia coli, Neisseria gonorrhoeae, Neisseria meningitidis, Pneumococcus, Hemophilis* influenzae B, *Treponema pallidum*, Lyme disease spirochetes, *Pseudomonas aeruginosa, Mycobacterium leprae, Brucella abortus, Mycobacterium tuberculosis, Tetanus*, a helminth, a malaria parasite, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus, Mesocestoides corti, Mycoplasma arthritidis, Mycoplasma hyorhinis, Mycoplasma orale, Mycoplasma arginini, Acholeplasma laidlawii, Mycoplasma salivarum, Mycoplasma pneumoniae*, or combinations of these pathogens.

The antibody used to form the conjugate may also recognize antigens associated with an autoimmune disease, such as idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, perniciousanemia, rapidly progressive glomerulonephritis, psoriasis, fibrosing alveolitis, and combinations of these autoimmune diseases.

The antibody selected to prepare the conjugate may also recognize an antigen associate with a cardiovascular disease. For example, the antibody may also be selected to recognize antigens associated with myocardial infarction, ischemic heart disease, atheroschlerotic plaques, fibrin clots, emboli, or a combination of these cardiovascular diseases. The antibody may also recognize an antigen specific for granulocytes, lymphocytes, monocytes, or a mixture of these cell types, where the presence of these cell types is indicative of cardiovascular disease.

The antibody or antibody fragment selected for preparing the conjugate may also specifically bind an antigen associated with a neurological disease, (e.g., the antibody or fragment may specifically bind antigens associated with an amyloid deposit).

The selected antibody or fragment used to prepare the conjugate may recognize an antigen associated with a multiple myeloma, a B-cell malignancy, a T-cell malignancy, or combinations of these diseases. Particular B-cell malignancies may include forms of B-cell lymphomas, aggressive forms of B-cell lymphomas, chronic leukemias, and acute lymphatic leukemias. Other malignancies may include non-Hodgkin's lymphoma or Hodgkin's lymphoma.

The antibody or fragment may also recognize an antigen associated with a solid tumor, including a melanoma, a carcinoma, a sarcoma, a glioma, or combinations of these solid tumors. Particular carcinomas include renal carcinomas lung carcinomas, intestinal carcinomas, stomach carcinomas, breast carcinomas, prostrate cancers, and ovarian carcinomas.

Cytokines or immunomodulators may also be selected to prepare the conjugate. Suitable cytokines or immunomodulators include IL-1, IL-2, IL-3, IL-6, IL-10, IL-12, IL-18, IL-21, interferon-α, interferon-β, interferonγ, G-CSF, and GM-CSF, or mixtures of these molecules.

In another embodiment of the method for preparing the conjugate, the method includes reacting a chelating agent and a protein to form the conjugate, and subsequently hydrolyzing any non-stable bonds formed between the chelating agent and the protein. Suitable methods for hydrolyzing the non-stable bonds may include chemical methods (e.g., treating the sample with a nucleophilic agent or adjusting the pH of the sample), however, other methods may be utilized as well (e.g., applying heat to the sample).

In a further embodiment of the method for preparing the conjugate, the method includes reacting a chelating agent and an acylating agent to form an activated chelating agent; reacting the activated chelating agent and a protein to form the conjugate; and reacting the conjugate and a quenching agent to hydrolyze any non-stable bonds.

Also disclosed herein is a conjugate prepared by the aforementioned methods, where the conjugate is substantially free of non-stable bonds between the chelating agent and the protein. For example, a conjugate prepared by the aforementioned method may be substantially free of non-amide bonds or ester bonds between the chelating agent and the protein. As such, the conjugate may incorporate a label (e.g., a radiolabel) very efficiently after the conjugate has been stored in solution for an extended period of time. Typically, a label will be incorporated with an incorporation yield of no less than about 97% when the label is reacted with a conjugate synthesized by the aforementioned methods, even after the conjugate is stored for no less than six months at about 4° C. In addition, because conjugates synthesized by the aforementioned methods are substantially free of non-stable bonds or ester bonds, typically no more than about 3% of the chelating agent is hydrolyzed from the conjugate, even after the conjugate is stored for no less than six months at about 4° C.

DETAILED DESCRIPTION OF THE PREFERRED EMBODIMENTS

In the following discussions, the more general term 'protein' is also understood to incorporate a category that includes proteins, polymers, polypeptides, and peptides. The proteins useful in the following processes may be antibodies (monoclonal or polyclonal), polymeric amino acids, cytokines, polypeptides, or peptides, or any protein that contains sufficient amine residues that can be acylated, in order to form a chelator-protein conjugate. The amine residues can be those naturally present in a protein chain (e.g., lysine or ornithine), or they can be amino groups placed within a protein chain artificially, (e.g., co-polymers such as KEPY). The described methods may be used for any synthesis method that includes conjugating a chelating agent (i.e., chelator) to an amino containing polymeric material using an acylation reaction on a free amino group. Proteins often contain groups other than amino groups that can be acylated during the amino acylation reaction. Such groups are most often hydroxyl- or thio- (mercapto) groups, but can be any functional group that can mimic the nucleophilic nature of the amino group. The inventors have found that attempts to attach chelating agents to proteins at amino groups (e.g., the ε-amino group of a lysine residue), may result in the production of amorphous products, wherein the chelating agents are also attached at other functional groups, (e.g., hydroxyl groups on residues such as tyrosine, threonine or serine; thiol groups of cysteine; and imidazoyl groups of histidine). This is undesirable and leads to unstable conjugates wherein a portion of the chelating agent is linked to the protein by bonds such as esters, thioesters, thiocarbamates, carbonates and thiocarbonates, etc., rather than a physiologically stable amide as desired.

Figure 3:
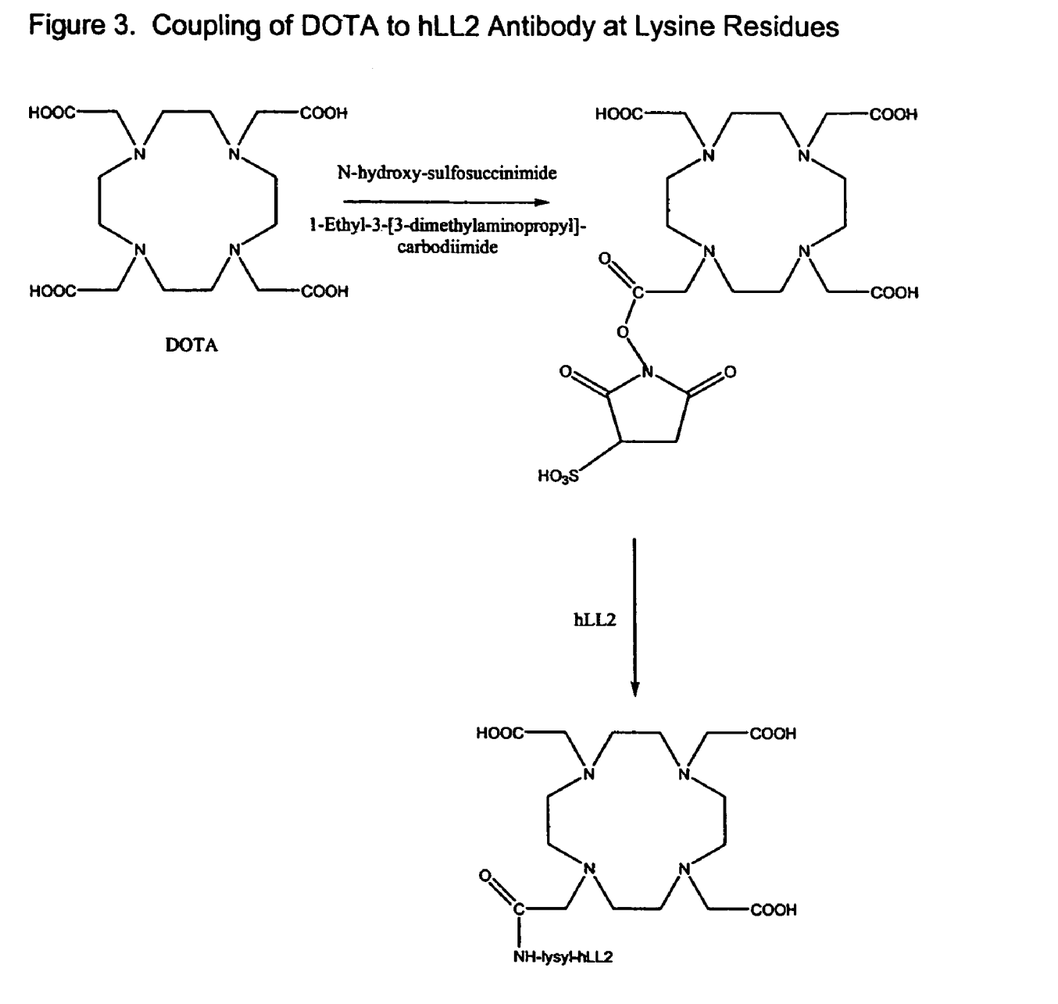
FIG. 3 is a schematic representation of a coupling reaction between DOTA and hLL2 antibody by activation of a carboxyl group on the DOTA and reaction with a lysine amino group on hLL2. The process may be carried out in a single step or in multiple steps.

Specifically, the inventors encountered the following problem in synthesizing a DOTA-MAb conjugate. See FIG. 3, Scheme 1. In this scheme, the chelating agent may be activated in situ and then used for protein coupling, but reaction schemes wherein the chelating agent intermediate is first separated and/or purified are also contemplated as within the scope of the present methods. When the activated chelating agent, in this case DOTA, is added to the multi-functional protein, in this case an antibody, the inventors found that a small percentage of the DOTA may couple not with an amino group, but with another residue(s), most likely tyrosine or threonine. Subsequently, when the DOTA-MAb was radiolabeled shortly after the DOTA-MAb conjugate was prepared, high yields (>90%) of either indium-111 or yttrium-90 could be incorporated into the conjugate. However, when the DOTA-MAb conjugate was stored for longer periods (>one month), incorporation yields of In-111 or Y-90 into the DOTA-MAb conjugate fell below 90%, and often fell over the initial one-to-six month period, post-preparation, to only 40-80%. Such a fall-off in radio-incorporation yields is undesirable because it requires that the radiolabeled DOTA-MAb conjugate must be purified prior to administration, to separate the desired conjugate product from low molecular weight products (e.g., In-111/Y-90 chelated to a hydrolyzed DOTA molecule). The purification step requires additional handling of radioactive materials and results in additional cost, and further, may result in the introduction of contaminants or may render the product commercially unviable.

The inventors hypothesized that the decrease in labeling yields was a result of disassociation of the DOTA from the MAb during storage. For example, the presence of a small amount of DOTA linked to the antibody by a non-amide bond, may lead, over time, in the aqueous environment in which the DOTA-MAb was stored, to a dissociation of that unstably bound DOTA. More specifically, that fraction of the DOTA that was conjugated to MAb on tyrosine, threonine, serine, or histidine residues by an ester or imidazoyl bond, may hydrolyze over time and release free DOTA into the DOTA-MAb solution. In turn, the slow accumulation of free DOTA in the DOTA-MAb solution may have lead to a competition of the free DOTA against the DOTA-MAb when the In-111 or Y-90 was admixed in the radiolabeling reaction. As such, the free DOTA may out-compete the DOTA-MAb for binding to radioactive label (i.e., In-111 and Y-90), and a mixture of In-111- or Y-90-DOTA and In-111-DOTA-MAb or Y-90-DOTA-MAb, respectively, may have resulted. The incorporation yields decreased over time, see Tables 1, 2, and 3, which is consistent with the slow hydrolysis of an ester or imidazoyl bond, over time, in an aqueous solution. The inventors tested their hypothesis by taking a sample of DOTA-MAb that had been shown to be efficiently radiolabeled when it was originally prepared. The sample of DOTA-MAb was then tested after it had been stored at approximately 2-8° C. for approximately 6 months. First, half of the stored sample was "repurified" by size-exclusion chromatography, thus removing any free DOTA that may have been liberated over time. The "repurified" and "non-repurified" fractions of the DOTA-MAb were then radiolabeled. The repurified fraction incorporated radiolabel with a yield of >90%, whereas the non-repurified fraction incorporated radiolabel with a yield of <80%. This suggests that the size-exclusion repurification step removes any free DOTA that forms over the storage period, and allows a near-full incorporation of radiometal into the DOTA-MAb, as when the DOTA-MAb conjugate was first synthesized.

By integrating a hydrolytic step into processes for making DOTA-MAb conjugates, any DOTA that is bound by unstable bonds can be removed prior to storage. Thus, after conjugation of the activated DOTA to the antibody, the conjugate is subjected to a short reaction with a nucleophilic agent or another agent to cleave or hydrolyze unstable bonds (e.g., heat or a pH change). This reaction (e.g., with a nucleophilic agent) ensures that any unstably bound DOTA (e.g., hydroxyl-linked DOTA) is cleaved from the DOTA-MAb conjugate, and only stably bound DOTA (e.g., amide-linked DOTA-MAb) remains bound to the conjugate in preparation for storage. This strategy has solved the problem of degradation of DOTA-MAb usefulness over extended storage times, allowing >95% incorporations of In-111/Y-90 into DOTA-MAb conjugates after shelf storage for greater than six months See Example 5, Table 3. It should be understood that unstable bonds (e.g., esters) can occur not only with conjugates prepared in situ, but also with conjugates prepared from chemically defined and separated intermediates. For instance, the use of a preformed active ester of the DOTA macrocycle could equally be expected to react with a certain percentage of available tyrosine or other reactive residues on a MAb. Additionally, the unwanted reaction may occur not only with active esters, but also with other activated intermediates, such as carbodiimides, isocyanates or isothiocyanates.

The described method may be useful for a variety of chelating agents and related peptide conjugates. Therapeutic and diagnostic chelating agents, peptides, chelator- (and/or chelate-) peptide conjugates, and methods for synthesizing such conjugates have been described. See U.S. Pat. No. 4,472,509; U.S. Pat. No. 4,678,667; U.S. Pat. No. 4,824,986; U.S. Pat. No. 4,831,175; U.S. Pat. No. 4,861,869; U.S. Pat. No. 5,057,302; U.S. Pat. No. 5,082,928; U.S. Pat. No. 5,082,930; U.S. Pat. No. 5,087,696; U.S. Pat. No. 5,099,069; U.S. Pat. No. 5,106,955; U.S. Pat. No. 5,112,953; U.S. Pat. No. 5,130,118; U.S. Pat. No. 5,217,704; U.S. Pat. No. 5,246,692; U.S. Pat. No. 5,271,927; U.S. Pat. No. 5,286,850; U.S. Pat. No. 5,310,535; U.S. Pat. No. 5,367,080; U.S. Pat. No. 5,434,287; U.S. Pat. No. 5,435,990; U.S. Pat. No. 5,612,016; U.S. Pat. No. 5,625,075; U.S. Pat. No. 5,739,323; U.S. Pat. No. 5,756,065; U.S. Pat. No. 5,756,685; U.S. Pat. No. 5,760,191; U.S. Pat. No. 5,808,003; *The peptides: Analysis, Synthesis, Biology*. E. Gross and J. Meienhofer, editors. Academic Press, NY, 1979; Brinkley M. *Bioconjugate Chem.*, 1992; 3:2-13; Carraway K L and Koshland D E, Jr., *Biochem Biophys Acta*, 1968; 160:272-274; Chinn PC, et al., *Int J Oncol.*, 1999; 15:1017-1025; Cummins CH, et al., *Bioconjug Chem.*, 1991; 2:180-186; Deshpande S V, et al., *J Nucl Med.*, 1990; 31:473479; Esteban J M, et al., *J Nucl Med.*, 1987; 28:861-870; Govindan S V, et al., *Bioconjug Chem.*, 1998; 9:773-782, Griffiths, et al., *J. Nucl. Med.*, 2003; 44:77-84; Harrison A, et al., *Nucl Med Biol Int J Radiat Appl Instrum Part B*. 1991; 5:469476; Hnatowich D J, et al., *J Immunol Methods*. 1983; 65:147-157, Kozak R W, et al., *Cancer Res.*, 1989; 49:2639-2644; Lewis M R, et al., *Bioconjug. Chem.*, 1994; 5:565-576, Li M, et al., *Bioconjug Chem.*, 1994; 5:101-104, Meares C F, et al., *Anal Biochem.*, 1984; 142:68-78, Sharkey R M, et al., *Int J Cancer*. 1990; 46:79-85; Stimmel J B, et al., *Bioconjug. Chem.*, 1995; 6:219-225; and Zoghbi S S, et al., *Int J Nuc Med Biol.*, 1985; 12:159-166, all of which are incorporated by reference in their entireties.

EXAMPLES

The invention is further illustrated by, though in no way limited to the following Examples.

Example 1

Preparation of a DOTA-Antibody Conjugate

The MAb used to form the DOTA-MAb conjugate was a complementarity-determining region-grafted [humanized] LL2 (hLL2; anti-CD22). LL2 antibodies are described in U.S. Pat. No. 5,789,544; U.S. Pat. No. 6,187,287; U.S. Pat. No. 2002-0102254, and U.S. application Ser. No. 10/446,689, all of which are incorporated by reference in their entireties.

a) Diafiltration of hLL2-IgG into DOTA conjugation buffer at room temperature: An Amicon stir cells unit was assembled, and 200 mL of MilliQ water was run through the unit, followed by a rinse with conjugation buffer (0.1 M $NaHCO_3$-0.1 M $K_2HPO_4$, pH 8.45). The unit was then filled to the 250 mL mark with conjugation buffer, and a 348-milligram portion hLL2-IgG was added to the buffer. The solution was concentrated to approximately 35 mL, during which time the progress of buffer-exchange was followed by monitoring pH and conductivity of the eluate from the stir cell unit at various times, and by comparing these values with those for the conjugation buffer itself. A duplicate diafiltration under identical conditions was also set up. The final combined diafiltered IgG was filtered through a pre-rinsed 60-mL acid-washed plastic syringe fitted with a 0.22 μm filter. Recovery from the 2 runs: 83 mL, 7.89 mg/mL or 655 mg. The sample was stored in a 250-mL acid-washed bottle (containing an acid-washed stir bar) at 4° C. until use.

b) DOTA activation: A solution of 1.212 g of DOTA (2.96 mmol) was dissolved in 20 mL of 0.4 M sodium bicarbonate (8 mmol), and stirred at 4° C. for 5 minutes to ensure complete dissolution. Then, 0.574 g of sulfosuccinimido-N-hydroxysuccinimide (2.645 mmol) was added, and dissolved by gently shaking. To this solution was added 0.753 mL of a freshly prepared 50 mg/mL, 0.26M aqueous solution of 1-ethyl-3-(dimethylaminopropyl) carbodiimide hydrochloride (EDC-HCl). The activation mixture was stirred at 4° C. for 45 minutes.

c) Conjugation reaction: The diafiltered hLL2-IgG solution was warmed to room temperature over 15 min during the DOTA activation (step 1, b). Next, the entire solution of activated DOTA was added in ten portions over a period of 1 minute. The molar ratio of activated DOTA to hLL2-IgG in the combined solution was ~45:1. The pH was adjusted from 7.37 to 8.24 with 1.2 mL of 1 N NaOH, added in 0.1 mL aliquots. The conjugation mixture was gently stirred at the ambient temperature (23° C.) for 2 h. The total volume of the reaction mixture was approximately 104 mL.

d) Quenching with hydroxylamine: The conjugation mixture was divided into 2 equal fractions (52 mL each) in 250-mL acid-washed bottles containing acid-washed stir bars. To one fraction was added 3.75 mL of 1.5 M hydroxylamine hydrochloride solution. The pH was re-adjusted from 6.83 to 8.0 with 3.5 mL of 1 N sodium hydroxide (final hydroxylamine conc.: 0.095M). The reaction was stirred for 1 hour. The second fraction was quenched with glycinamide, as a different quencher than hydroxylamine. The two quenched fractions were processed similarly, as described further below for the hydroxylamine-treated conjugate.

e) Ammonium sulfate precipitation: After quenching, the fraction was mixed with 60 mL of saturated ammonium sulfate and stirred gently for 30 minutes. The precipitated solution was centrifuged (3° C.-5° C.) at 5000 RPM for 10 minutes, and at 4200 RPM for a further 20 minutes. The supernatant was decanted, and the pellet resuspended in 120 mL of 50% ammonium sulfate and centrifuged at 5000 RPM for 30 minutes. The resuspension and centrifugation steps were repeated once more. The final pellet was dissolved in 60 mL of 0.25 M ammonium acetate pH 5.5, and the sample was stored at 4° C. overnight (~18 h).

f) Diafiltration of the product in storage buffer at room temperature: Diafiltrations were carried out by first diluting the final product (of step 1, e) to 350 mL, with 0.25 ammonium acetate, pH 5.5. The product was then concentrated to approximately 50 mL. The dilution-concentration steps were repeated twice more. The product was then concentrated to approximately 25 mL, and sterile-filtered into 50-mL acid-washed sterile centrifuge tubes. Recovery: 33.5 mL, 8.97 mg/mL (300 mg).

Example 2

Preparation of a DOTA-Antibody Conjugate

The antibody used to form the DOTA-MAb conjugate was hPAM4, which is an anti-MUC-1 antibody. See U.S. application Ser. No. 10/461,885 filed Jun. 16, 2003 and Ser. No. 60/388,314 filed Jun. 14, 2002, both of which are incorporated by reference in their entireties.

a) Diafiltration of hPAM4-IgG into conjugation buffer at room temperature: A 350 mL Amicon stir cell unit was assembled and 200 mL of MilliQ water was run through the unit followed by a rinse with conjugation buffer. The unit was then filled to approximately 250 mL with conjugation buffer. A portion of hPAM4-IgG (250 mg) was added. The volume was brought to 350 mL, and the solution then concentrated to approximately 25 mL. The diafiltered IgG was filtered through a pre-rinsed 60-mL acid-washed plastic syringe fitted with a 0.22 µm filter into an acid-washed vial. Recovery: hPAM4-IgG~29 mL, 7.4 mg/mL or 214 mg. The sample was stored in a 50-mL acid-washed vial at 4° C. until use.

b) DOTA activation: A solution of 258.1 mg of DOTA (0.639 mmoL) and 138.7 mg of sulfosuccinimido-N-hydroxysuccinimide (0.639 mmoL) in 4.8 mL of 0.4 M sodium bicarbonate (1.92 mmol) was prepared and gently shaken to ensure complete dissolution. To this solution was added 0.164 mL (0.0426 mmoL) of a freshly prepared 50 mg/mL, 0.26M aqueous solution of 1-ethyl-3-(dimethylaminopropyl) carbodiimide hydrochloride. The activation mixture was stirred at 4° C. for 45 minutes.

c) hPAM4 Conjugation: To the diafiltered hPAM4-IgG was added 4.96 mL (42.64 µmoL) of activated DOTA solution, (from step 2, b, above). The molar ratio of activated DOTA to hPAM4-IgG in the combined solution was ~30:1. The pH was adjusted from 8.21 to 8.40 with 0.07 mL of 1 N sodium hydroxide. The conjugation mixture was stirred at ambient temperature (23° C.) for 2 h. Total volume: 33.1 mL.

d) Quenching of the DOTA/hPAM4 conjugation reaction: A solution of 1.5 M Hydroxylamine (2.61 g/25 mL) was prepared in conjugation buffer as described above, and the pH was adjusted from 4.5 to 8.1 with 6.1 mL 6N sodium hydroxide. The conjugation reaction (step 2, c) was quenched by addition of 2.38 mL of the 1.5 M hydroxylamine solution, (final concentration 0.1M hydroxylamine). The mixture was stirred gently for 1 h at room temperature. Total volume, 35.5 mL.

e) Ammonium sulfate precipitation: The quenched reaction was mixed with an equal volume (35.5 mL) of saturated ammonium sulfate and stirred gently for 30 minutes. The precipitated solution was centrifuged at 5000 RPM for 30 minutes (4° C.); the supernatant decanted; and the pellet resuspended in 71 mL of 50% ammonium sulfate. This mixture was then centrifuged at 5000 RPM for 25 minutes. The resuspension and centrifugation steps were repeated once more. The final pellet was dissolved in 40 mL of 0.25 M ammonium acetate (pH 5.5) and stored at 4° C. overnight (~18 h).

f) hPAM4-DOTA diafiltration: The conjugate sample was diluted to 350 mL with 0.25M sodium acetate, pH 5.5, in a 350 mL stir-cell unit and concentrated to 25 mL. The process was repeated twice more bringing the volume to ~20 mL at the last diafiltration. The diafiltered DOTA-hPAM4 was then filtered through a 0.22 µm filter into an acid-washed polypropylene tube. Total recovery of DOTA-hPAM4 conjugate was approximately 23.5 mL; at a concentration of 7.85 mg/mL.

Example 3

Figure 1:
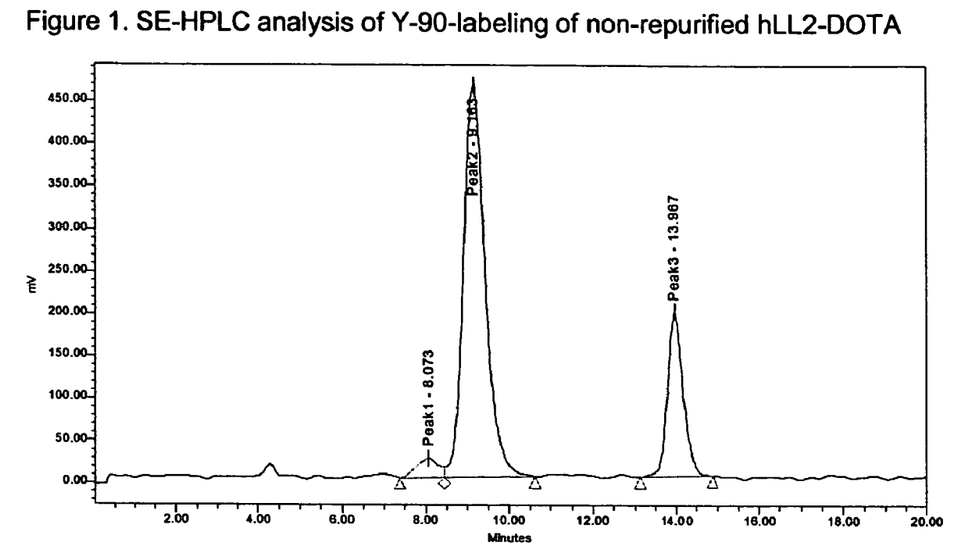
FIG. 1 is a graphic representation of an SE-HPLC analysis of Y-90-labeling of non-repurified hLL2-DOTA.
Figure 2:
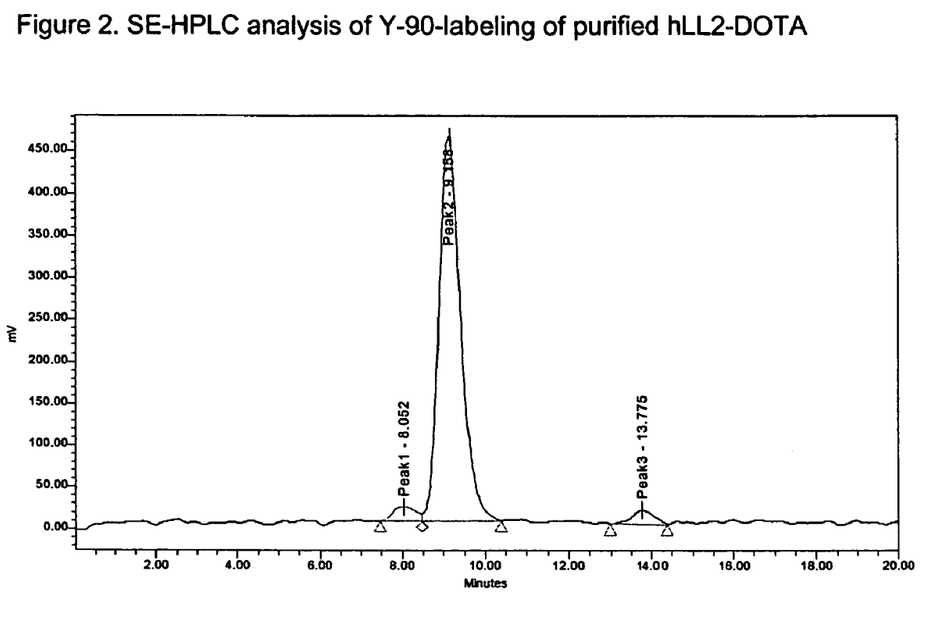
FIG. 2 is a graphic representation of an SE-HPLC analysis of Y-90-labeling of purified hLL2-DOTA.

Y-90 Radiolabeling of a 6-Month Old Lot of DOTA-hLL2 Prepared Without Hydroxylamine Treatment, and Comparison with Y-90 Radiolabeling of the Same Lot of DOTA-hLL2 After Repurification a) Repurification of DOTA-hLL2: The radiolabeling was performed in the same manner for both "repurified" and "non-repurified" DOTA-MAb conjugate. An initial volume of 1.4 mL (12 mg) of DOTA-hLL2 (originally manufactured, approximately 6 months earlier, by a process that did not involve quenching with hydroxylamine), was split into two 0.7 mL (6 mg) portions. One portion was repurified by passage through a 3-mL size centrifuged size-exclusion column of Sephadex G50/80® equilibrated in 0.25 M ammonium acetate, pH 5.4. The second 0.7 ml fraction was tested without repurification. Both samples were radiolabeled with Y-90, as described in 3 b), below.

b) Y-90 radiolabeling of repurified and non-repurified DOTA-hLL2: Y-90 chloride from Perkin-Elmer life Sciences (Billerica, Mass.), ~6 mCi, was buffered with 0.2 mL of 0.25 M ammonium acetate, pH 5.4. Aliquots (0.1 mL) of buffered Y-90 were added to each of the two samples, (from part 3 a, above). Sample 1 contained 2.57 mCi of Y-90, and sample 2 contained 2.50 mCi of Y-90. Samples were incubated at 45° C. for 1 hr, to allow Y-90 radiolabeling, and then treated with 0.08 mL of 0.1 M aqueous DTPA for 10 minutes at the same temperature to scavenge any non-DOTA-hLL2-bound Y-90. Radiolabeled samples were analyzed in two distinct chromatographic systems. The samples were analyzed either by ITLC (instant thin-layer chromatography) on silica gel-impregnated glass fiber strips (Gelman Sciences, Ann Arbor, Mich.), developed in 10 mM EDTA, or by SE-HPLC (size-exclusion high performance liquid chromatography) using 0.2 M sodium phosphate/0.02% sodium azide, pH 6.8, at 1 a mL/minute flow rate. See FIGS. 1 and 2. The ITLC results indicated a >96% incorporation of Y-90 into DOTA-hLL2 that had been repurified, and only a 81% incorporation of Y-90 into DOTA-hLL2 that had not been repurified. See Table showing % INCORPORATION, below.

| | % INCORPORATION | | |
|---|---|---|---|
| | ITLC | SE-HPLC | |
| | (% MAb Bound) | IgG Bound | Low MW |
| hLL2-DOTA (non-purified) | 81.1% | 77.5% | 22.5% |
| hLL2-DOTA (repurified) | 96.3% | 96.5% | 3.5% | c) Conclusion: Some low molecular weight material (such as free DOTA), was removable by size exclusion chromatography. The amount of this low molecular weight material in the vial lot of hLL2-DOTA increased during storage. This low molecular weight material was able to bind to Y-90 added during radiolabeling, and inhibit full binding of added Y-90 to the DOTA-hLL2 conjugate. Thus, a certain percentage of the DOTA may be dissociated or detached or from the antibody during the storage period, which is consistent with a small percentage of the attached chelating agent originally being bound by unstable bonds (e.g., esters of hydroxyl groups), rather than by stable bonds (e.g., amides of amine groups).

Example 4

Incorporation Yields of Y-90 into Samples of DOTA-hLL2 and DOTA-hMN-14 Prepared without the Use of a Quenching Reaction

TABLE 1

| Shelf Time (months) | HPLC: Y-90-DOTA-hLL2 (%) | HPLC: Free Y-90 (%) | ITLC: Free Y-90 (%) |
|---|---|---|---|
| Lot i) 0 | 98.3-98.4 | 1.6-1.7 | 1.4 |
| 3 | 92.8-92.9 | 7.1-7.1 | 5.8-6.3 |
| 6 | 86.6-88.9 | 11.2-13.4 | 10.0-10.0 |
| Lot ii) 0 | 96.7-97.7 | 3.2-3.4 | 2.8-3.6 |
| 3 | 94.8-94.7 | 5.2-5.3 | N.D. |
| 6 | 88.0-88.6 | 11.4-12.0 | 11.1-11.1 |
| 12 | 84.2-84.3 | 15.8-15.8 | 13.6-13.8 |
| Lot iii) 0 | 94.5-94.5 | 5.2-5.5 | 5.0-5.4 |
| 1 | 85.6-88.8 | 11.2-14.4 | 9.1-12.5 |
| 2 | 88.3-88.8 | 11.3-11.6 | 8.3-9.2 |
| 3 | 87.2-87.9 | 12.1-12.9 | 12.2-12.8 |
| 5 | 86.6-87.3 | 12.7-13.4 | 11.7-12.4 |
| 6 | 83.9-84.2 | 15.8-16.1 | 15.6-19.0 |
| Lot iv) 0 | 96.4-97.1 | 2.6-6.0 | 2.2-3.0 |
| 1 | 93.3-95.6 | 5.6-7.3 | N.D. |
| 3 | 90.3-95.2 | 6.3-9.8 | N.D. |
| 5 | 92.4 | 7.6 | N.D. |
| 6 | 86.7-90.7 | 9.3-13.3 | 8.4-11.5 |
| 9 | 91.6-91.6 | 8.4-8.4 | N.D. |
| 13 | 78.9-88.5 | 12.0-21.1 | N.D. | a) Table 1. Incorporation yield of Y-90 into several distinct lots of DOTA-hLL2. Samples of DOTA-hLL2 and DOTA-hMN-14 were prepared according to example 1) above. The % incorporation is shown for radiolabeling the DOTA-hLL2 at times indicated post-manufacture (shelf time=time since manufacture date). No quenching step was used in the manufacture. Data is shown in average percent incorporations with analyses performed in triplicate or duplicate, except as marked* (N.D.=not done).

TABLE 2

| Shelf Time (months) | HPLC: Y-90-DOTA-hMN-14 (%) | HPLC: Free Y-90 (%) | ITLC: Free Y-90 (%) |
|---|---|---|---|
| Lot i) 0 | 98.1-98.6 | 1.6-1.9 | 1.7-1.8 |
| 3 | 94.1-94.1 | 5.8-6.0 | N.D. |
| 6 | 93.0-93.1 | 6.9-7.0 | N.D. |
| 9 | 92.7-92.7 | 7.3-7.3 | N.D. |
| 12 | 87.7-89.9 | 10.2-12.3 | N.D. |
| Lot ii) 0 | 97.8-98.8 | 1.6-2.5 | 1.3-1.9 |
| 2 | 96.2-97.8 | 2.3-3.8 | 2.4-3.8 |
| 4 | 92.5-92.5 | 7.5-7.5 | N.D. |
| 6 | 91.4-91.8 | 8.2-8.6 | N.D. |
| 9 | 90.1-90.9 | 9.2-9.9 | N.D. |
| 12 | 88.9-89.1 | 11.0-11.2 | N.D. |
| Lot iii) 0 | 96.9-97.9 | 2.0-3.1 | 2.3-3.5 |
| 1 | 94.8-95.0 | 5.0-5.2 | N.D. |
| 2 | 94.9-95.2 | 4.9-5.1 | 5.2-5.3 |
| 3 | 91.5-92.1 | 8.0-8.5 | 7.1-7.3 |
| 6 | 94.2-96.0 | 4.0-5.8 | N.D. |
| 12 | 93.7-94.1 | 5.9-6.3 | 5.1-5.1 | b) Table 2. Shown are the results of radiolabeling several distinct lots of DOTA-hMN-14 conjugate at times indicated post-manufacture (shelf time=time since manufacture date). No quenching step was used in the manufacture of the conjugate. Data is shown in average percent incorporations with analyses performed in triplicate or duplicate, except as marked* (N.D.=not done).

Example 5

Time-Course Radiolabeling Analyses of the DOTA-hLL2 Conjugate of Example 1, (Prepared by a Process Including Treatment with Hydroxylamine).

TABLE 3

| Shelf Time (months) | HPLC: Y-90-DOTA-hLL2 (%) | HPLC: Free Y-90 (%) | ITLC: Free Y-90 (%) |
|---|---|---|---|
| 0 | 99.5-99.5 | 0.5-0.5 | 1.1-1.2 |
| 1 | 98.3-98.4 | 1.6-1.7 | 2.3-2.4 |
| 2 | 98.6-99.0 | 1.0-1.4 | 1.7-1.8 |
| 3 | 97.2-97.4 | 2.6-2.8 | 1.2-1.8 |
| 6 | 99.0-100 | 0.0-1.0 | 1.0-1.0 |
| 12 | 97.8-99.0 | 1.0-2.2 | 1.4-2.4 |

Table 3. Incorporation yields of Y-90 into samples of DOTA-hLL2, prepared according to example 1) above, using an incubation of the freshly-prepared conjugate with hydroxylamine, to "quench" the unstable ester bonds being formed during the DOTA-to-antibody conjugation reaction:

All patients and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

It will be readily apparent to one skilled in the art that varying substitutions and modifications may be made to the invention disclosed herein without departing from the scope and spirit of the invention. For example, a variety of different binding pairs can be utilized, as well as a variety of different therapeutic and diagnostic agents. Thus, such additional embodiments are within the scope of the present invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

What is claimed is:

1. A method of preparing a conjugate comprising:
   a first step (a) of reacting a DOTA chelating agent and a protein to form the conjugate at an alkaline pH; and
   a second step (b) of reacting the conjugate formed in step (a) with a quenching agent at an alkaline pH; wherein the quenching agent is hydroxylamine or salt thereof.

2. The method of claim 1, wherein the conjugate is formed by an amino acyl reaction.

3. The method of claim 1, wherein the chelating agent is activated by reaction with an acylating reagent prior to reacting the chelating agent and the protein to form the conjugate.

4. The method of claim 1, further comprising radiolabeling the conjugate with $^{47}$Sc, $^{51}$Mn, $^{52}$Mn, $^{52}$Fe, $^{59}$Fe, $^{55}$Co, $^{62}$Cu, $^{64}$Cu, $^{67}$Cu, $^{67}$Ga, $^{68}$Ga, $^{72}$As, $^{77}$As, $^{83}$Sr, $^{89}$Sr, $^{86}$Y, $^{89}$Zr, $^{90}$Y, $^{94}$Tc, $^{94}$mTc, $^{99}$Mo, $^{99}$mTc, $^{105}$Pd, $^{105}$Rh, $^{111}$Ag, $^{110}$In, $^{111}$In, $^{123}$I, $^{124}$I, $^{125}$I, $^{131}$I, $^{142}$Pr, $^{143}$Pr, $^{149}$Pm, $^{153}$Sm, $^{154-58}$Gd, $^{161}$Tb, $^{166}$Dy, $^{166}$Ho, $^{169}$Er, $^{175}$LU, $^{177}$Lu, $^{186}$Re, $^{188}$Re, $^{189}$Re, $^{194}$Ir, $^{197}$Pt, $^{198}$Au, $^{199}$Au, $^{211}$At, $^{211}$Pb, $^{212}$Bi, $^{212}$Pb, $^{213}$Bi, $^{223}$Ra, or $^{225}$Ac.

5. The method of claim 1, wherein said protein comprises an antibody, an antibody fragment, a cytokine or immunomodulator, a polyprotein, or mixtures thereof.

6. The method of claim 5, wherein said protein is a monoclonal or polyclonal antibody.

7. The method of claim 6, wherein the antibody is murine, chimeric, primatized, humanized, or human in origin.

8. The method of claim 5, wherein the antibody or antibody fragment is multispecific.

9. The method of claim 5, wherein the antibody or antibody fragment is bi-specific.

10. The method of claim 5, wherein the antibody or antibody fragment is multivalent.

11. The method of claim 1 further comprising reacting the conjugate with a metal ion.

12. The method of claim 1, wherein said conjugate contains four or less DOTA chelating agent moieties and one protein moiety.

* * * * *